United States Patent
Lim, Sr.

(10) Patent No.: US 10,806,436 B2
(45) Date of Patent: Oct. 20, 2020

(54) VENTED SPECIMEN RETRIEVAL BAG

(71) Applicant: Roger R. Lim, Sr., Dallas, TX (US)

(72) Inventor: Roger R. Lim, Sr., Dallas, TX (US)

( * ) Notice: Subject to any disclaimer, the term of this patent is extended or adjusted under 35 U.S.C. 154(b) by 326 days.

(21) Appl. No.: 15/983,825

(22) Filed: May 18, 2018

(65) Prior Publication Data

US 2019/0167243 A1   Jun. 6, 2019

Related U.S. Application Data

(60) Provisional application No. 62/593,503, filed on Dec. 1, 2017.

(51) Int. Cl.
| | | |
|---|---|---|
| *A61B 17/00* | (2006.01) | |
| *A61B 10/00* | (2006.01) | |
| *A61B 10/04* | (2006.01) | |
| *A61B 10/02* | (2006.01) | |

(52) U.S. Cl.
CPC .... *A61B 17/00234* (2013.01); *A61B 10/0096* (2013.01); *A61B 10/04* (2013.01); *A61B 2010/0208* (2013.01); *A61B 2017/00287* (2013.01); *A61B 2217/005* (2013.01)

(58) Field of Classification Search
CPC .......... A61B 17/00234; A61B 10/0096; A61B 10/04; A61B 2010/0208; A61B 2017/00287; A61B 2217/005; A61B 2017/221; A61B 2017/2212; A61B 2017/2215; A61B 2017/2217; A61B 17/32056
USPC ........................................................ 600/562
See application file for complete search history.

(56) References Cited

U.S. PATENT DOCUMENTS

| | | |
|---|---|---|
| 6,350,267 B1 | 2/2002 | Stefanchik |
| 6,406,440 B1 | 6/2002 | Stefanchik |
| 8,172,772 B2 | 5/2012 | Zwolinski et al. |
| 9,005,215 B2 | 4/2015 | Grover et al. |
| 9,033,995 B2 | 5/2015 | Taylor et al. |
| 9,364,202 B2 | 6/2016 | Menn et al. |
| 9,649,147 B2 * | 5/2017 | Gilbert ............... A61B 18/1233 |
| 2006/0200169 A1 | 9/2006 | Sniffin |
| 2011/0190781 A1 * | 8/2011 | Collier ............. A61B 17/00234 606/114 |
| 2015/0282821 A1 * | 10/2015 | Look ...................... G06Q 30/02 606/127 |
| 2015/0320409 A1 * | 11/2015 | Lehmann ......... A61B 17/00234 600/109 |

* cited by examiner

*Primary Examiner* — David J. McCrosky
*Assistant Examiner* — Chanel J Jhin
(74) *Attorney, Agent, or Firm* — Pearl Cohen Zedek Latzer Baratz LLP

(57) ABSTRACT

Vented specimen retrieval bag assists in removal of air and fluid around a specimen so that a specimen pouch can be compressed around a specimen and removed from a smaller incision during surgery. Removal of air and fluid may be active, by way of vacuum, or by passive venting.

13 Claims, 4 Drawing Sheets

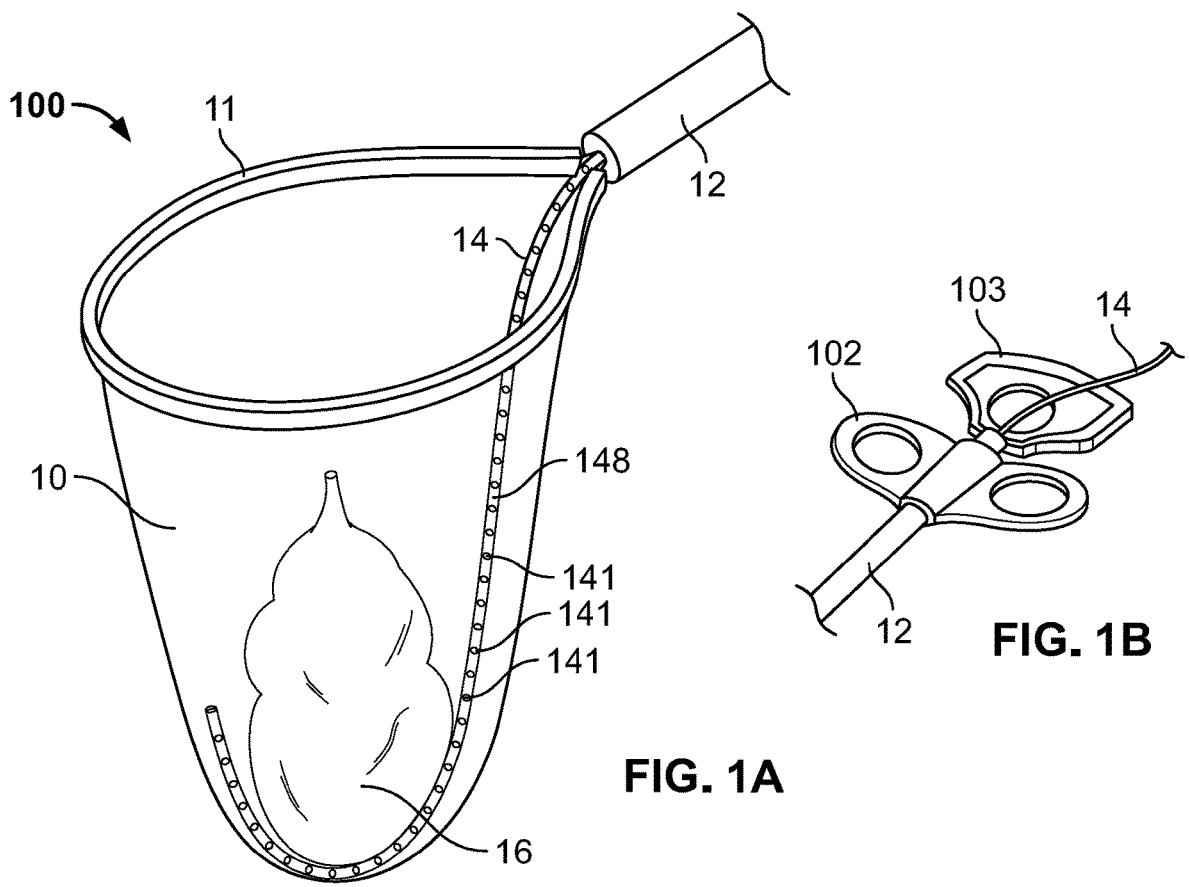
FIG. 1A
FIG. 1B
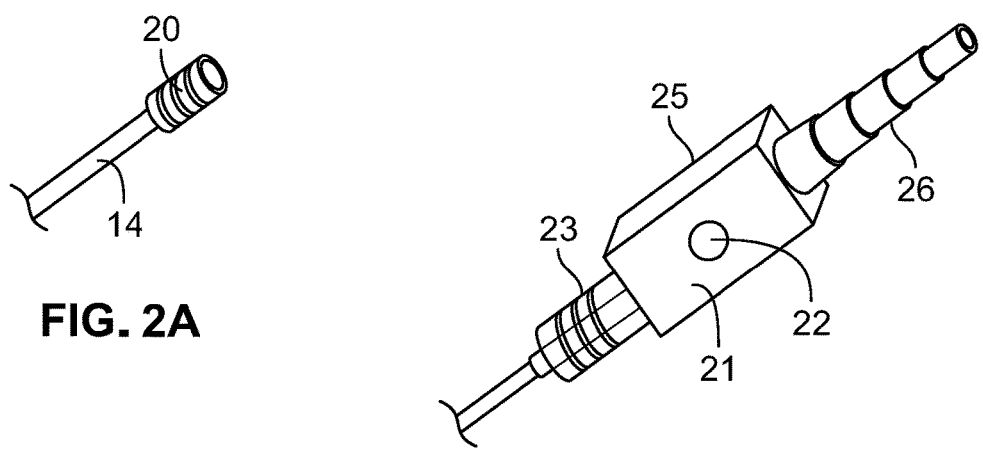
FIG. 2A
FIG. 2B

VENTED SPECIMEN RETRIEVAL BAG

CROSS REFERENCE TO RELATED APPLICATIONS

This application claims priority to U.S. Provisional Application No. 62/593,503 filed on Dec. 1, 2017, which is incorporated herein by reference in its entirety.

FIELD OF THE INVENTION

The present invention relates to a surgical apparatus and, in particular, to a specimen retrieval apparatus for removing tissue or an organ from a patient during surgery. The specimen retrieval apparatus according to the invention includes a specimen retrieval bag provided with means to withdraw trapped air and fluid around a specimen within the bag and compress the bag around the specimen to facilitate removal from an incision in a patient. In embodiments, the device is provided with a vented suction regulator which can be manipulated by the user to control the amount of suction provided to the inside of the bag.

BACKGROUND OF THE INVENTION

Increasingly, surgical techniques require smaller and smaller surgical openings. With improvements in endoscopic and laparoscopic procedures, a problem has arisen with conventional specimen retrieval bags, in that fluids and air pockets created in the specimen bag cause a challenging extraction. When a surgeon attempts to pull the bagged specimen from the surgical cavity, fluids and air pockets trapped in the bag with the specimen prevent the extraction because the size of the specimen bag with the specimen in it is too large to be extracted from the opening.

U.S. Pat. No. 6,406,440, which is incorporated by reference, discloses a technique, and a specimen bag adapted for the technique, for transferring a portion of tissue being removed from a patient from a part of the specimen removal bag inside the patient to a part outside the patient during the specimen removal process. However, this technique only partly addresses the problem caused by entrapped fluids and air around the specimen and does not leverage the use of suction.

U.S. Pat. No. 9,005,215, which is also incorporated by reference, discloses a specimen retrieval apparatus incorporating a vacuum tube in the handle and at least partially in the bag. However, the vacuum tube is not adapted to close and compress the bag around the specimen, as only a single suction opening is provided on the tube, and the vacuum is not integrated with the bag.

U.S. Pat. No. 8,172,772, which is also incorporated by reference, discloses a specimen retrieval device which also uses vacuum to remove fluids from the specimen bag. This device likewise suffers from too little control over how the bag compresses around the specimen when vacuum is applied and creates a potential for specimen leakage.

U.S. Pat. No. 9,364,202, which is also incorporated by reference, proposes a vented specimen removal device including openings which vent into the body cavity. This only partially resolves the problem of trapped air and fluids around the specimen, because of positive pressure in the body cavity where the bag is "vented" and therefore, among other disadvantages, does not provide for sterile collection.

There remains an unmet need in the art for a specimen removal bag which can be fully and efficiently evacuated of air and other fluids around the specimen and compressed around the specimen to provide the smallest possible size for removal.

Thus, an object of the invention is to provide means for extracting fluids or air pockets from a specimen bag using negative pressure during the specimen removal process, either actively (with suction) or passively (with venting), to compress the specimen bag while extracting the specimen from the body cavity so that smaller incisions can be used and extractions can be completed safely and collection can be done in a sterile manner.

SUMMARY OF THE INVENTION

These and other objects of the invention are achieved with a vented specimen retrieval apparatus according to the present invention which, in one aspect, comprises: a proximal handle; a flexible specimen bag attached to a distal end of the proximal handle, having an open proximal end for receiving a specimen and a closed distal end. A distal ring is supported by the handle and supports the flexible specimen bag. A tube extends within the proximal handle configured for connection at a proximal end of the tube to a source of negative pressure. A plurality of channels positioned in the specimen bag in fluid communication with the tube are configured to withdraw fluids (including air) from the bag so that the specimen bag closes around a specimen in the bag from the distal end to the proximal end when negative pressure is applied to the tube. Using the apparatus according to the invention, the size of the specimen bag with the specimen in it will get smaller as greater suction is applied and extraction of the specimen from the cavity will be facilitated. Various configurations for distributing the suctioning around the specimen are contemplated herein.

A method of using the apparatus according to the invention includes inserting the apparatus described above through an incision in a patient, such as during a laparoscopic or endoscopic procedure. The ring supporting the specimen bag, initially inside the proximal handle when the specimen retrieval apparatus is inserted through the incision, may be deployed inside the patient using instrument handles on the proximal end of the handle. The user guides a specimen into the open end of the specimen bag and draws a draw string tight around the proximal end of the specimen bag, again using instrument grips on the proximal end of proximal handle. Suction is applied, and air or any specimen fluid is extracted from the bag so that the specimen bag closes around the specimen. Fluid that is suctioned can be drained outside the patient, or collected in a sterile specimen container (Lukens trap) at the end of the vented suction connector if desired. The smaller sized specimen and bag, with the air and fluids removed, may then be removed from the patient.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 1A depicts a distal end of a specimen retrieval apparatus according to an embodiment of the invention, including the specimen bag;

FIG. 1B depicts a proximal end of an apparatus according to embodiments of the invention, including the proximal handle;

FIG. 2A depicts a female luer lock on a suction line adapted for connection to a suction regulator according to the invention;

FIG. 2B depicts a suction regulator according to embodiments of the invention;

DETAILED DESCRIPTION OF THE INVENTION

The terms "tissue" and "specimen" are used broadly herein to refer to any biological material to be removed from a patient via an incision. Thus, "tissue" may refer to a tumor or a tissue portion intended for biopsy, and a "specimen" may refer to any tissue, organ or any part thereof.

As used herein, "distal" means toward and into the patient, into the surgical incision, and into the interior of the specimen bag. Conversely the "proximal" direction is the opposite direction, toward the open end of the bag and toward the user of the instrument.

A specimen retrieval apparatus according to the invention includes a specimen retrieval bag or pouch supported on the distal end of a proximal handle. The bag comprises at least one wall formed from a flexible material, which may be made from, for example, vinyl, nylon, latex, polyurethane, polyethylene, polypropylene, silicone, or other material known in the art to have sufficient strength at a thickness of 1 to 5 mils to retain a specimen without undesired deformation, and yet having sufficient flexibility to become compressed around the specimen when vacuum is applied.

In some embodiments, as discussed in the following detailed description, the apparatus comprises a second or "inner" bag, which may be porous, i.e., comprising a mesh or having perforations. The second bag may be located inside a nonporous outer bag forming a space between the inner bag and the outer bag to which vacuum can be applied. The materials for the second bag may be selected from the same class of thin, flexible and sufficiently strong plastic materials as the outer layer. The inner bag may be attached to the outer bag at points, with adhesive, ultrasonic bonding or the like.

A proximal handle comprises an elongated hollow tube of stainless steel or the like for supporting the specimen retrieval bag at the distal end. In embodiments, the tube accommodates a wire for operating a drawstring around the open proximal end of the specimen retrieval bag, operable to close the bag around the specimen. Various configurations of finger loops on the proximal end of the handle may be provided, as known in the art, to enable a user to manipulate the bag inside the incision, to close the bag around the specimen, and to perform other manual operations discussed herein.

The ring supporting the specimen bag according to the invention may be deployed from inside the hollow handle as disclosed in U.S. Application Publication 2006/0200169, which is incorporated by reference. A shape memory metal, such as Nitinol may be used for this purpose to make the ring, in association with springs so that the pouch is operable to be opened by the user during a procedure, as known in the art.

Figure 6A:
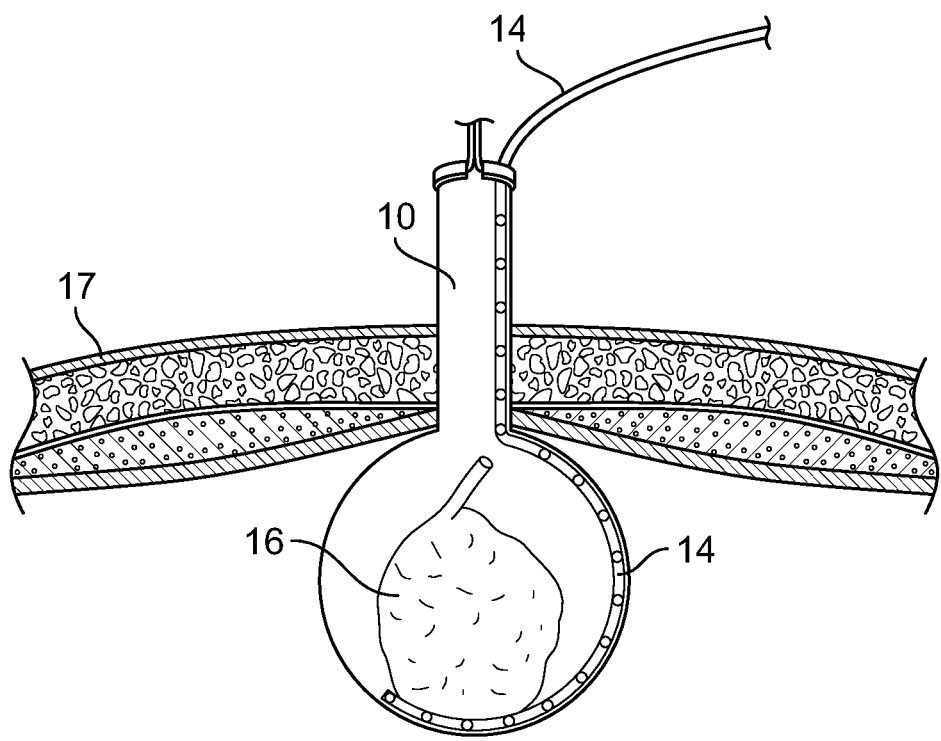
FIG. 6A and FIG. 6B depict different stages of specimen removal with a specimen retrieval apparatus according to an embodiment of the invention.
Figure 6B:
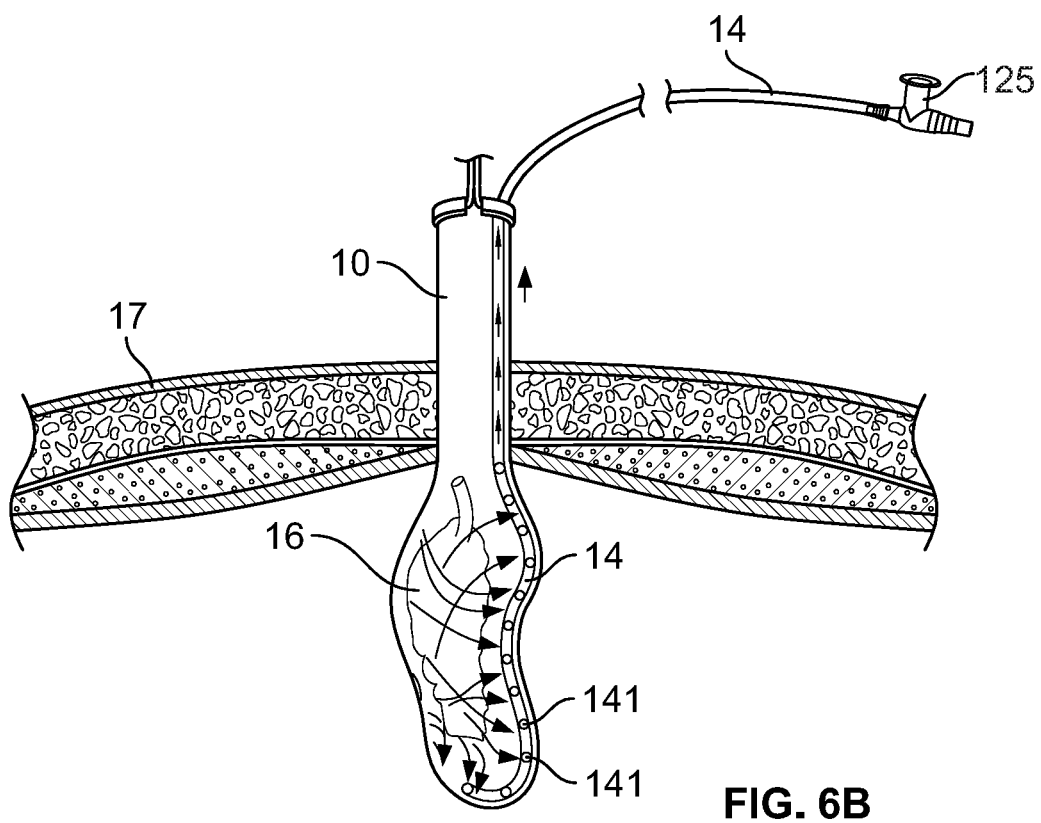

In embodiments, a suction line is threaded through the hollow handle and is connected to a plurality of channels positioned in the distal end of the specimen bag and in fluid communication with the suction line, and with a source of negative pressure. The channels may take the form of apertures in a tube. The tube inside the bag may have round cross section or have a flattened configuration. In embodiments, a tube connected to a source of negative pressure extends from the end of the proximal handle and the distal end of the tube and contains a plurality of apertures or channels connected to the source of negative pressure. The tube is preferably (but not necessarily) attached to, or formed integrally with, the specimen bag (as seen in FIGS. 6A and 6B). Attachment may be done with an adhesive, ultrasonic bonding or any other method known in the art, or the tube may be extruded with the bag. In embodiments, a plurality of such tubes, each having a plurality of apertures may stem from the same tube extending from the proximal handle. In use, the channels or apertures are located proximate the specimen, to facilitate closing the bag around the specimen in a compact manner. Specific embodiments for surrounding the specimen with a source of negative pressure are disclosed below.

The tube may be connected to a source of negative pressure with intermediate devices using tubing connectors and/or luer type connectors. For example, in embodiments, a stopcock may be provided between a female luer lock connector provided on the end of the tubing of the suction line and a male luer lock on the suction regulator as described below. A syringe can be used on the stopcock to flush fluids or air from, and/or aspirate into, the vented specimen retrieval bag. In embodiments, a suction regulator attachment is provided having an opening on one end operatively connected to the bag, an opening on the other end attached to the source of negative pressure, and a vented opening between the two ends to regulate the amount of suction applied to the bag and specimen.

Specific embodiments, which are not to be deemed limiting of the invention are described in the Examples below.

FIG. 1A is a detail of a distal portion of a specimen retrieval apparatus 100 according to an embodiment of the invention, including proximal handle 12, distal ring 11 and specimen bag 10 supported on distal ring 11. A tube 14 is threaded through proximal handle 12 and may be attached to the bag. Distal end of the tube 14 extends from handle 12 and includes a plurality of apertures 141. During a laparoscopic procedure, when specimen 16 is trapped in bag 10, apertures 141 are proximate specimen 16. Tube 14 may have a circular or flattened cross-section.

Figure 3:
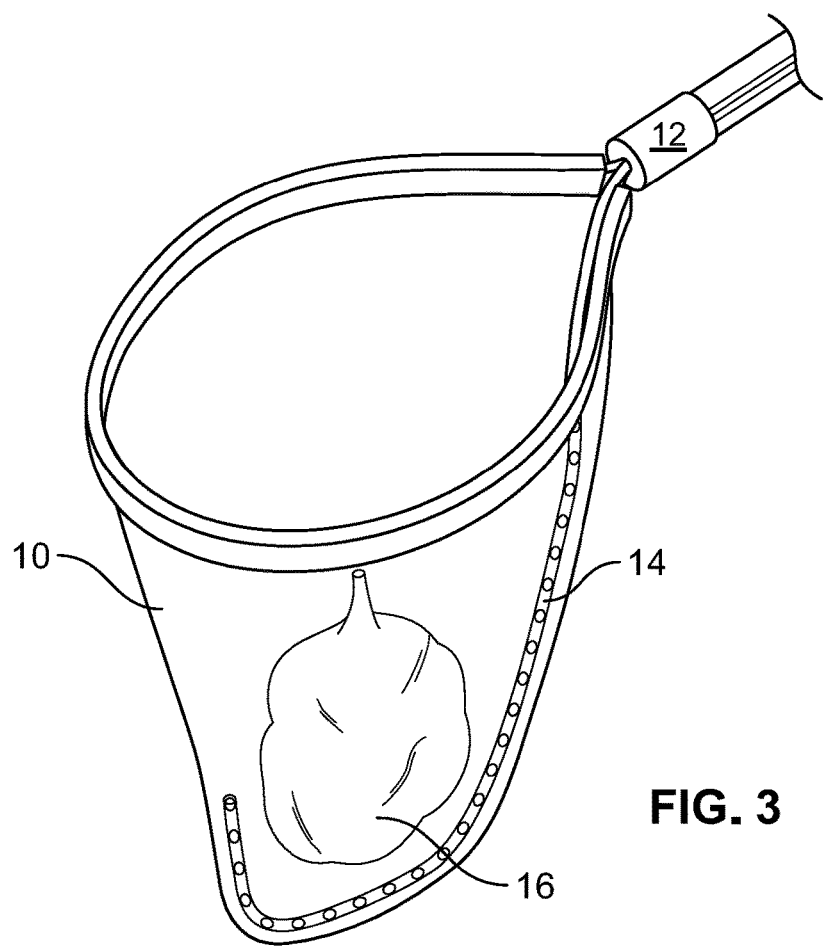
FIG. 3 is a detail of the specimen bag at the distal end of the proximal handle according to an embodiment of the invention.

FIG. 1B is a detail of a proximal end of the specimen retrieval apparatus 100, including finger loops 102, 103 for manipulating the instrument during a surgical procedure. As shown best in a phantom view in FIG. 3, tube 14 is threaded into proximal handle 12 and then extends from proximal handle for attachment to a source of negative pressure (suction line).

As shown in FIG. 2A tube 14 of the suction line may be provided with female luer lock 20 at the end of tube 14 for connection to male luer lock connector 23 which is integral with suction regulator 25 according to the invention. As seen in FIG. 2B, suction regulator 25 has a built-in male luer lock 23 connector, which may be formed integrally with the regulator for attachment to the female luer lock connector 20. Suction regulator 25 includes vent 22 to regulate the amount of negative pressure applied to the tube 14 and bag 10. Vent 22 is an opening which may be closed off by a user during a surgical operation to increase the amount of suction. The opening may be adapted to conform to a user's finger, for example, or a closure may be provided to variably increase and decrease the size of the opening. Such details may be left to the skill of the artisan. Suction regulator 25 is provided with a conventional tubing connector 26 for connection to a source of negative pressure.

Figure 4:
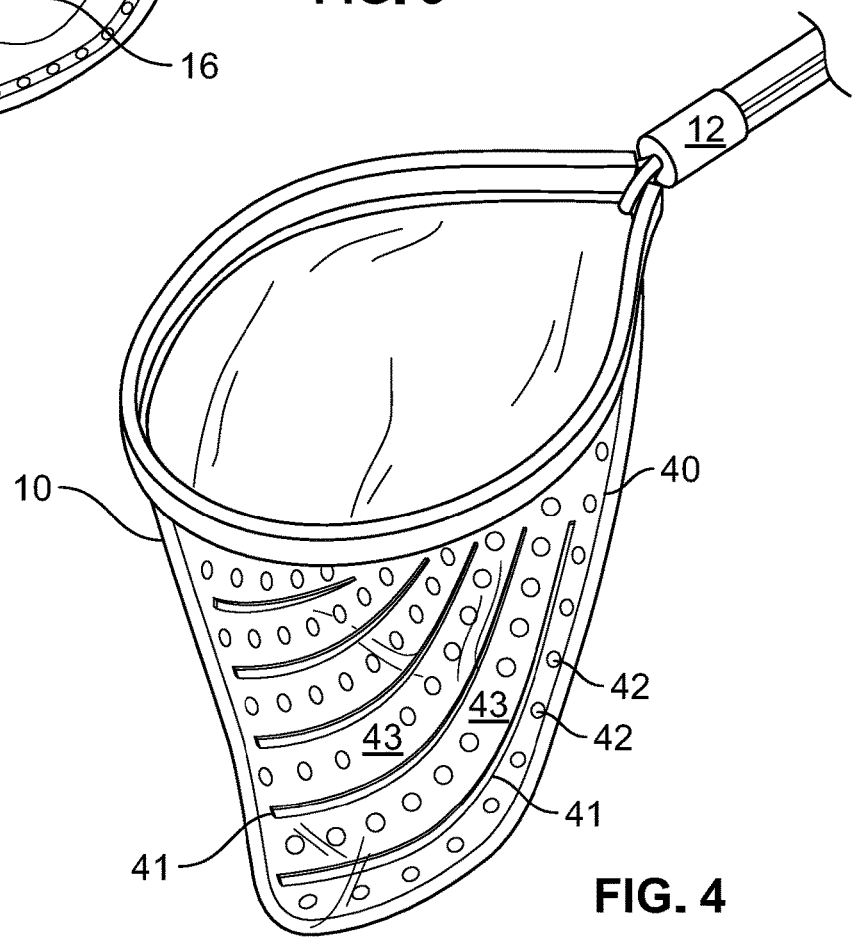
FIG. 4 is another detail of the specimen bag at the distal end of the proximal handle according to another embodiment of the invention.

FIG. 4 depicts a double walled specimen bag according to another embodiment of the invention, wherein a porous inner bag 40 is positioned inside of the specimen bag 10. Inner bag 40, is provided with a plurality of holes 42. Suction is applied via tube 14 to a space between the inner bag 40 and outer specimen bag 10. A plurality of channels 43 is formed in the space between the walls 10 by a series of ridges 41. The channels are configured to direct air and fluid toward the suction tube 14. Ridges 41 may be formed so as to be integral with the outer bag, integral with the inner bag, or may physically bridge the outer bag and the inner bag, so outer bag 10 is connected to inner bag 40 via ridges 41.

Figure 5:
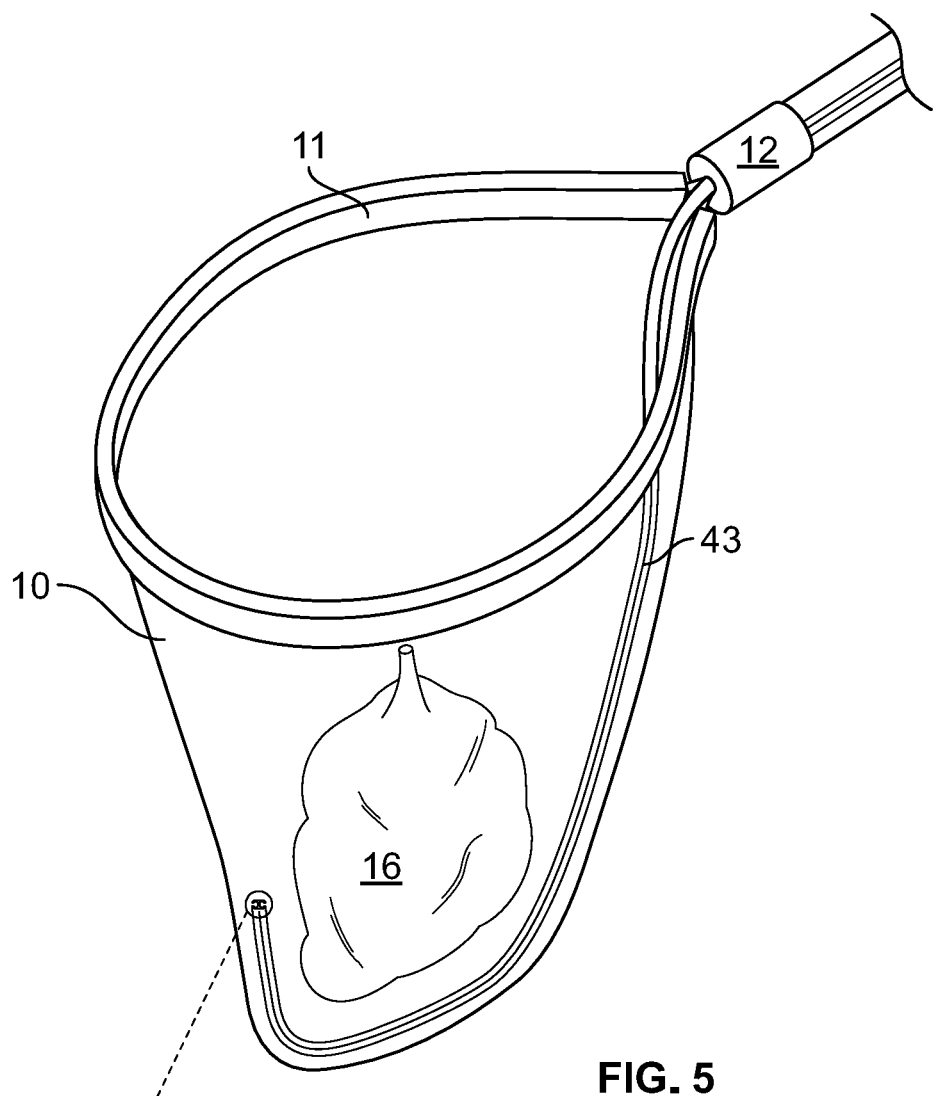
FIG. 5 is another detail of the specimen bag at the distal end of the proximal handle according to yet another embodiment of the invention.
Figure 5A:
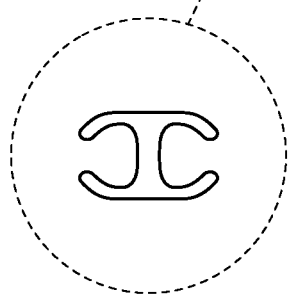

FIG. 5 depicts an alternative embodiment wherein a channel is formed by an open channel drain 43 connected to a source of negative pressure. As with the tube 14 of FIG. 1, channel drain 43 may be circular or flattened in cross-section and is positioned to optimize the closing of bag 10 around the specimen 16.

FIG. 6A and FIG. 6B schematically show how the specimen bag is reduced in size and withdrawn from an incision in the patient's skin 17 after air is withdrawn from a plurality of apertures or channels in the tube 14 to reduce the size of the specimen and the bag when suction is applied. The plurality of channels 141 ensure that the specimen 17 is tightly compacted when suction is applied. The tube is shown attached to the side of the bag in FIGS. 6A and 6B according to preferred embodiments of the invention. As shown in FIG. 6B, a suction regulator 125 may be provided with tubing connectors to assist in applying the suction, but preferred embodiments include a suction regulator having a vent and a built-in male luer lock connector as depicted in FIG. 2B, and as discussed above.

To use the specimen retrieval apparatus according to the invention during a laparoscopic or endoscopic procedure, the distal end of the apparatus 100 is inserted into an incision in the patient. At this stage, ring 11 supporting the specimen bag is initially inside the proximal handle when the specimen retrieval apparatus is inserted through the incision. The ring 11 is deployed inside the patient using instrument handles 102, 103 on the proximal end of the handle. The user guides a specimen 16 into the open end of the specimen bag 10 and draws a draw string tight around the proximal end of the specimen bag, again using instrument grips 102 or 103 on the proximal end of proximal handle 12. Suction is applied, and air or any specimen fluid is extracted from the bag so that the specimen bag closes around the specimen. Fluid that is suctioned can be drained outside the patient, or collected in a sterile specimen container (Lukens trap) at the end of the vented suction connector if desired. The smaller sized specimen and bag, with the air and fluids removed, may then be removed from the patient.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

Features of the invention described with reference to one embodiment may be combined with a different embodiment without departing from the scope of the invention. Likewise, a feature set forth in a dependent claim may be combined with a different independent or dependent claim(s) without departing from the scope of the invention. Reference may be made to the United States patent documents cited herein to describe technical features and materials known in the art to be used for similar devices. Absent specific indication to the contrary, steps in a method according to the present invention may be performed in any order, and two steps may be performed simultaneously.

What is claimed is:

1. A surgical specimen retrieval apparatus, comprising:
a proximal handle;
a flexible specimen bag attached to a distal end of the proximal handle, having an open proximal end and a closed distal end;
a distal ring supported by the handle and supporting the flexible specimen bag;
a tube extending within the proximal handle configured for connection at a proximal end of the tube to a source of negative pressure; and
a plurality of channels positioned in the specimen bag in fluid communication with the tube, configured to withdraw fluid from the bag so that the specimen bag closes around a specimen in the bag from the distal end to the proximal end when negative pressure is applied to the tube;
wherein the specimen bag comprises an outer nonporous bag and an inner porous bag, wherein space between the outer nonporous bag and the inner porous bag is in fluid communication with the source of negative pressure, and wherein the plurality of channels comprises channels between the nonporous outer bag and the porous inner bag directing airflow generated from the source of negative pressure in a direction toward the source of negative pressure.

2. The surgical specimen retrieval apparatus according to claim 1, further comprising a draw string closure around the open proximal end of the specimen bag, operable from the proximal handle to be closed around a specimen in the specimen bag.

3. The surgical specimen retrieval apparatus according to claim 1, wherein the tube extends from the distal end of the proximal handle to the distal end of the specimen bag, and wherein the plurality of channels consists of a plurality of apertures positioned along the tube, and wherein each aperture of said plurality of apertures is in fluid communication with the source of negative pressure.

4. The surgical specimen retrieval apparatus according to claim 3, comprising a plurality of tubes in fluid communication with the source of negative pressure, each tube of said plurality of tubes extending from the proximal handle toward the distal ends of the specimen bag and each comprising a plurality of apertures in fluid communication with the source of negative pressure.

5. The surgical specimen retrieval apparatus according to claim 1, wherein said channels between the nonporous outer bag and the porous inner bag are formed by ridges formed on the inner surface of the nonporous outer bag.

6. The surgical specimen retrieval apparatus according to claim 5, wherein the ridges are connected to the porous inner bag as well as the nonporous outer bag.

7. The surgical specimen retrieval apparatus according to claim 1, further comprising a suction regulator having an integral male luer lock connector on one side adapted for attachment to a female luer lock connector on the tube; a tubing connector on another side of the suction regular adapted for connection to the source of negative pressure; and an opening adapted to be open, closed or partially open to regulate suction.

8. The surgical specimen retrieval apparatus according to claim 1, further comprising a stopcock operatively connected to the source of negative pressure, and a syringe operatively connected to the stopcock, adapted to flush fluids and air from the tube and/or aspirate fluids and air into the specimen bag.

9. The surgical specimen retrieval apparatus according to claim 1, comprising at least one elongated open channel in communication with the source of negative pressure, extending to the distal end of the specimen bag.

10. The surgical specimen retrieval apparatus according to claim 1, comprising a drain within the bag connected to the source of negative pressure.

11. A method for removing a surgical specimen from a patient, comprising:
   inserting an apparatus according to claim 1 through an incision in a patient; guiding a tissue specimen into the open end of the flexible specimen bag of said apparatus;
   applying negative pressure to withdraw air and fluids through a plurality of channels positioned in a distal portion of the specimen bag around the specimen to reduce the size of the bag containing the specimen;
   closing a drawstring around the open end of the specimen bag; and
   removing the specimen and the bag from the incision.

12. A method according to claim 11, comprising draining or collecting fluid from a stopcock located between the tube extending within the proximal handle of said apparatus and the source of negative pressure.

13. A method according to claim 11, comprising opening, closing or partially closing a vent operatively connected to the tube and the source of negative pressure to regulate suction applied in the tube.

* * * * *